United States Patent
Mönch

[19]

[11] Patent Number: 6,044,855
[45] Date of Patent: Apr. 4, 2000

[54] DEVICE AND METHOD FOR RINSING CHANNELS OF MEDICAL INSTRUMENTS

[75] Inventor: Harry Mönch, Knittlingen, Germany

[73] Assignee: Richard Wolf GmbH, Knittlingen, Germany

[21] Appl. No.: 08/968,620

[22] Filed: Nov. 12, 1997

[30] Foreign Application Priority Data

Nov. 12, 1996 [DE] Germany ............. 196 46 584

[51] Int. Cl.⁷ ...................................... B08B 3/00
[52] U.S. Cl. .................. 134/169 R; 134/166 R; 134/167 R; 134/22.12
[58] Field of Search ............... 134/51, 166 R, 134/167 R, 167 C, 169 C, 166 C, 22.1, 22.11, 22.12, 169 R; 422/100, 103

[56] References Cited

U.S. PATENT DOCUMENTS

| | | | |
|---|---|---|---|
| 1,999,571 | 4/1935 | Nickerson | 134/166 R |
| 2,636,502 | 4/1953 | Buechel | 134/166 R |
| 2,764,992 | 10/1956 | Reynolds et al. | 134/167 R |
| 2,783,765 | 3/1957 | Hagedorn | 134/167 R |
| 3,963,438 | 6/1976 | Banez | 21/58 |
| 4,278,101 | 7/1981 | Tanaka et al. | 134/167 C |
| 4,299,244 | 11/1981 | Hirai | 134/102 |
| 4,337,223 | 6/1982 | Kaye | 422/112 |
| 4,522,223 | 6/1985 | Balsys et al. | 137/240 |
| 4,526,622 | 7/1985 | Takamura et al. | 134/21 |
| 4,537,209 | 8/1985 | Sasa | 134/166 C |
| 4,576,650 | 3/1986 | Yabe et al. | 134/22.12 |
| 4,667,691 | 5/1987 | Sasa | 134/169 C |
| 5,090,433 | 2/1992 | Kamaga | 134/169 C |
| 5,143,105 | 9/1992 | Katayama | 134/167 C |
| 5,408,991 | 4/1995 | Iida et al. | 128/4 |
| 5,443,801 | 8/1995 | Langford | 422/294 |
| 5,476,454 | 12/1995 | Campbell | 604/283 |
| 5,487,376 | 1/1996 | Yabe et al. | 600/121 |
| 5,494,530 | 2/1996 | Graf | 134/18 |
| 5,543,119 | 8/1996 | Sutter et al. | 422/299 |
| 5,678,584 | 10/1997 | O'Brien | 134/166 R |
| 5,755,894 | 5/1998 | Bowman et al. | 134/22.12 |
| 5,795,403 | 8/1998 | Biermaier | 134/22.12 |
| 5,795,404 | 8/1998 | Murphy et al. | 134/22.12 |
| 5,840,251 | 11/1998 | Iwaki | 422/36 |
| 5,882,589 | 3/1999 | Mariotti | 422/28 |

FOREIGN PATENT DOCUMENTS

| | | | |
|---|---|---|---|
| 678206 | 1/1964 | Canada | 134/167 C |
| 44 40 363 | 5/1996 | Germany . | |

Primary Examiner—Frankie L. Stinson
Assistant Examiner—Paul J. Lee
Attorney, Agent, or Firm—Cohen, Pontani, Lieberman & Pavane

[57] ABSTRACT

The invention is concerned with a device and a method for cleaning and disinfecting medical instruments, in particular instruments of minimal invasive surgery (MIS). Instead of the rigid connection of cleaning tubings to instrument connections and exits which has been used up to now and which have the disadvantage that certain contaminated regions remain inaccessible for a secure cleaning, there is suggested a docking of injector nozzles in defined chronological intervals, the injector nozzles being fixed in a centric position to the openings of the instrument connections. At the same time various types of injector nozzles are applied for adaptation to various instrument connections and openings. By measuring the rinsing fluid quantity flowing to the instrument connections and the total discharging rinsing fluid quantity, the quality of preparation may be evaluated and documented.

14 Claims, 5 Drawing Sheets

DEVICE AND METHOD FOR RINSING CHANNELS OF MEDICAL INSTRUMENTS

BACKGROUND OF THE INVENTION

The invention relates to a device for rinsing channels of medical instruments with fluid, the device comprising an injector nozzle which in shape and position is adapted or adaptable to a respective instrument connection, at least one fluid supply to the injector nozzle as well as a fluid operating device, and relates to a rinsing method in which such a device is employed.

With a known device of this type, rinsing and injector devices are provided for cleaning and rinsing through the hollow bodied instruments of minimal invasive surgery (MIS). With this, several instruments or instrument shanks may be deposited obliquely in rows with several connections for rinsing. There are further variously shaped injector nozzles or connection adaptors available for the different connections of the medical instruments which may be selectively used with the known device. Common to all injector nozzles and connection adaptors is that for rinsing the instruments they are rigidly connected to the connections or shank ends thereof.

Due to reasons of hygiene a mechanized preparation by way of rinsing the instruments is required since only thus can a standardization in the preparation be ensured. A manual preparation at the same time should be avoided if possible. Many instruments are designed such that contaminated regions are very difficult to access for preparation. Thus for the mechanized preparation, cleaning and disinfection devices are necessary, these permitting an optimum preparation result. The term "preparation" covers the cleaning as well as the disinfection of the instrument, and the term "fluids" includes, but is not limited to, liquids, gases and steams.

The accesses to endoscopic instrumentation are designed as connector connections and serve the expansion or adaptation and are formed as introductions or passages for gripping instruments, sampling and excession forceps, scissors as well as other auxiliary instruments and additional accessories, or are used as supply and removal tubing systems. At the same time the connections are formed as Luer connections, plug connectors, threaded connections, bayonet connections and likewise, these representing all easily releasable connections.

If medical instruments, in particular instruments of minimal invasive surgery, are to be applied for the mechanized preparation for cleaning and disinfection of the instrument channels, then up to now all accesses and connection openings must be manually rigidly connected to tubing systems so that a controlable rinsing of the channels can be ensured. These rigid connections however prevent the required cleaning and disinfection in the region of the adaptation so that bacteria, viruses and germs remain as rest matter and may be transmitted to patients. Present remaining impurities such as blood remains and secretions at high temperatures in automatic preparation machines are even coagulated in very critical, relatively inaccessible regions and thus form an additional large risk.

The tubing conduits and adaptors used with known rinsing devices are not always suitable for the specifically targeted and qualifiable preparation (cleaning and disinfection), since due to the pushing over of a tubing or with screw connections or part connections, no complete preparation may be effected in the covered regions. Thus there is an increased risk of transmitting germs.

BRIEF SUMMARY OF THE INVENTION

It is therefore the object of the invention, with a device of the known type for rinsing channels of medical instruments with fluid, to allow even critical regions at the connections of instruments to be accessible during the whole preparation, and that a temporary docking in the form of a conclusive connection and with a defined pressure force may be program controlled. It is further the object of the invention to specify a method for rinsing channels of medical instruments with the device according to the invention such that a secure preparation of different instrument types as well as a certifiable evaluation of the preparation quality are possible.

The above mentioned first object part is achieved with a device of the previously described type in that each injector nozzle comprises a plunger which is movingly guided in the axial direction in an injector hollow cylinder and which at its distal end is adapted to the shape of the associated instrument connection and which is so operable by fluid guided in the hollow cylinder that the instrument channel to be rinsed in each case is sealed to the outside at the connection concerned.

With a preferably provided adjusting device the height as well as the angular position of the injector nozzle may be infinitely adjusted with regard to a stationary holder and may be rigidly clamped with a squeezing screw connection. Thus in a simple manner the required adaptation of the injector nozzle or its plunger movement centrally to the inlet of the instrument channel to be rinsed in each case can be achieved.

The plunger consists of a soft elastic material so that its distal end, during which the plunger is pushed forward to the instrument during the rinsing procedure and is pushed into the bore of the instrument channel or pressed on the instrument connection, creates a connection which securely seals the instrument channel to be rinsed towards the outside.

In the plunger, an axial passage channel which tapers conically towards the distal end of the plunger injects, when the distal end is pressed into the bore or is pressed onto the connection, rinsing fluid into the instrument channel or removes fluid from this channel.

According to the invention the injector nozzle may basically be formed in two embodiments:

a) a first embodiment form in which the rinsing fluid flow is simultaneously the control fluid acting on the plunger in its cylinder. This embodiment form of the injector nozzle is only to be applied for the rinsing fluid injection into the instrument to be prepared; and b) a second embodiment form in which the rinsing fluid and the control fluid flow are separated in the injector nozzle. This is formed such that the control fluid flow, as with the first embodiment example, may flow to the control space of the injector nozzle through a first fluid supply and that the rinsing fluid flow is guided through a separate rinsing fluid tube which intersperses the control space and communicates with the passage channel of the plunger and is surrounded by this. With this second embodiment form one end of the rinsing fluid tube protruding from the hollow cylinder forms a connection which connects the rinsing fluid tube to a reservoir for the rinsing medium via a connecting conduit.

Common to the two above mentioned embodiment forms a) and b) of the injector nozzle according to the invention is that the plunger at its retrograde end region guided in the hollow cylinder comprises a circumferential sealing lip of soft elastic material which forms a seal between the plunger and the inner wall of the hollow cylinder and by way of this seals the control space towards the outside. In order to increase the efficiency of the control fluid supplied under pressure, the plunger at its retrograde end comprises a concave and centrically symmetrical recess into whose center the passage channel opens or with the embodiment b) is in connection with the rinsing fluid tube. This centric recess may advantageously form a spherical recess at the end of the plunger.

Furthermore a compression spring is so arranged in the hollow cylinder that the spring presses back the plunger into the cylinder when the fluid pressure in the control space is interrupted.

After unscrewing a cap which is screwed onto the end of the hollow cylinder and which closes the end of the hollow cylinder, the plunger axially movable in the hollow cylinder is easily accessible, exchangeable and can be replaced by other plunger types.

Advantageously the personnel operating the device according to the invention have different types of plunger at their disposal, according to the type and shape of the connections of the medical instruments to be prepared.

It is further provided that the complete injector nozzle can be exchanged wherein it is preferably easily releasably coupled to the adjusting device. Due to the exchangeability of the plunger and/or the injector nozzles, all components of the device according to the invention may again be separately and simply prepared.

With a method for rinsing channels of medical instruments with the device according to the invention, achieving the second part of the above mentioned object
a) there are provided injector nozzles which in their number and the shape of their respective plungers, are adapted to the instrument connections of the instrument to be rinsed;
b) the injector nozzles are fixed to the floor of a rinsing basket with a clamping device;
c) connecting conduits are fixed between the fluid operating device and the fluid admission of each injector nozzle as well as, where appropriate, between the rinsing fluid tube and a collector channel;
d) the instrument is itself fixed and the height and alignment of each injector nozzle is adjusted and is clamped with the squeezing screw connection so that the plunger is centric to the rinsing channel opening of the instrument;
e) the fluid operating device is so operated in a time controlled manner, that by way of this the plunger or plungers with its or their distal end is or are pressed into the channel opening or onto the periphery of the rinsing channel connection;
f) finally the instrument channels are rinsed in chronological intervals via the injector nozzles, wherein at least one instrument channel is brought into connection with the collector channel.

In order to control the injector nozzles in defined chronological intervals, i.e. to supply with fluid pressure, there is provided a time control device 200, shown by way of example in FIG. 3, which is connected to the fluid operating device of a rinsing machine or cleaning machine and which carries out a time controlled step by which means the injector nozzles are operated in the defined chronological intervals for rinsing through the instrument channels.

The time control unit may be program controlled such that a preparation program adapted to a certain instrument to be prepared may be selected. The rinsing device according to the invention is preferably a part of each individual instrument receiving container.

For cleaning an endoscopic instrument, it is placed into a rinsing basket, wherein the position of the instrument is unambiguously fixed by way of corresponding receptacles and fastening means and the connection pieces of the instrument are centrically aligned with regard to the injector nozzles fastened in the rinsing basket.

Each injector nozzle comprises at the proximal end of its fastening part a tubing or connection which is connected in the rinsing machine to corresponding connecting or distributing connection pieces.

The rinsing basket equipped with the instrument is placed into the rinsing machine, and tubings protruding from the respective rinsing basket are connected to corresponding connection pieces within the rinsing machine.

Corresponding to the program course of the fluid operating device of the cleaning machine, the cleaning, disinfection and/or sterilisation of the instrument and its channels are effected in given time intervals, selectively with one another or in chronological intervals after one another.

In order to also clean, disinfect and/or sterilize the regions of the annular bearing of the conical plunger of the injector nozzles applied by way of the control or rinsing fluid on the instrument connection piece, the rinsing time of the channels should be shorter than the rinsing time of the instrument from the outside, or after the rinsing of the channels, additionally a rinsing of the outer surface of the instrument should follow.

During the cleaning of the outer instrument parts and surfaces, the previously mentioned conical plunger of the respective injector nozzle is located at a certain distance from the connection pieces of the instrument. Thus the opening of the respective instrument connection opening can also be reached by the rinsing fluid given the surface cleaning of the instrument.

If, in accordance with the present invention, it has been ascertained that, the supplied quantity of rinsing liquid on rinsing the instrument is trapped by the collector channel, the quality of preparation may be evaluated on the basis of the total rinsing fluid quantity which has flowed to the instrument and the discharged quantity of rinsing liquid trapped in the collector channel. For this, the rinsing fluid quantity flowing to each individual instrument channel may be individually measured and recorded.

BRIEF DESCRIPTION OF THE DRAWINGS

Further features of the invention are specified in the dependent claims and are partly also described in more detail hereinafter by way of the embodiment examples shown in the drawing. There are shown in each case perspectively and partly in section:

DETAILED DESCRIPTION OF THE INVENTION

Figure 1:
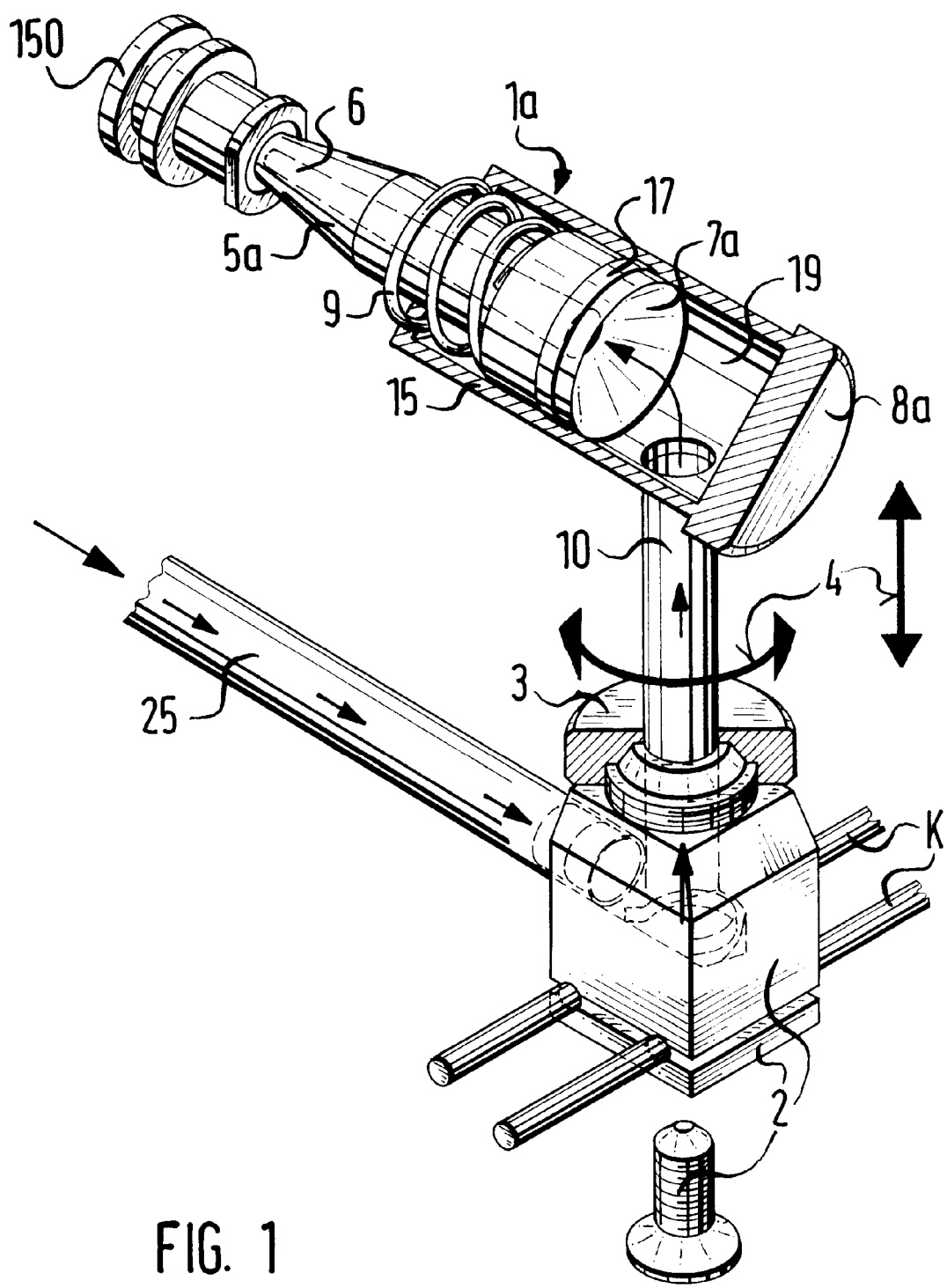
FIG. 1 a first embodiment form of the rinsing device according to the invention in which the rinsing liquid flow acts also as a control fluid flow, FIG. 2 a second embodiment form of the rinsing device according to the invention in which the rinsing fluid flow is supplied or removed separately from the control fluid flow, FIG. 3 a first application example of a rinsing device according to the invention and according to FIG. 1, FIG. 4 a second application example in which the rinsing device according to FIG. 1

Referring now to FIG. 1, a first embodiment of the present invention is indicated generally at 1*a*. In the first embodiment, which the rinsing fluid supplied to the injector nozzle acts simultaneously as a control fluid. The rinsing fluid identical to the control fluid may be any fluid which is used in the field of preparation of surgical instruments, such as e.g. a disinfection means, water steam or likewise. The term "preparation" used in the context of this application means that the instruments are cleaned and disinfected. Thereafter a sterilisation in steam or gas is effected.

FIG. 1 shows only a section of a rinsing device according to the invention with an injector nozzle docked onto an instrument connection 150. This part of the rinsing device is required in each case for one connection of the instrument. Furthermore for certain connections on the instrument, i.e. for example on the shank tube end, the second embodiment form of the injector nozzle indicated at 1b in FIG. 2 may also be docked. The rinsing device must be placed such that the plunger 5a stands centrically aligned to the channel opening of the connection. For this the rinsing device is firstly fixed on a wire floor of a rinsing basket K shown only schematically, with the help of a fastening and clamping device 2.

Into the fastening device 2 there opens a fluid admission 25, and a fluid supply 10 connected to the injector nozzle is coupled to the fastening device 2 adjustably in height and in a rotatable manner. A clamping device 3 serves to fix the height and rotational position of the injector nozzle connected to the fluid supply 10. In this way the angular and height position of the injector nozzle can be infinitely adjusted (see arrow 4) and fixed to the device 3 formed as a squeezing screw connection. The injector nozzle of the rinsing device 1a is formed by the plunger 5a which is axially displaceably guided in an injector hollow cylinder 15.

The plunger 5a is, with the first embodiment form according to FIG. 1, conically tapered towards the distal end and consists of a soft elastic material (e.g. silicon rubber). The conical distal end of the plunger 5a should in its shape and dimensions in each case be adapted to the instrument connection. It is therefore advantageous when the plunger 5a, within the cylinder, is easily exchangeable with another having other dimensions.

The plunger 5a further comprises an axial centrically lying passage channel 6 which conically tapers towards the distal end and which forms the nozzle channel of the injector nozzle. At its retrograde end the plunger 5a has a spherical recess 7a into which the channel 6 centrally opens. In the inside of the hollow cylinder 15 between the recess 7a and the inner wall of a screw cap 8a there is formed a control space 19 into which opens the fluid supply 10. Furthermore the plunger 5a at one end comprises a circumferential lip 17 which seals the control space 19 towards the outside. This lip 17 consists of softer elastic material than the plunger 5a itself.

In FIG. 1 the rinsing fluid circuit and the control fluid circuit are identical. The fluid is supplied via the admission 25 opening at the fastening device 2. By way of the pressure acting on the rear wall of the plunger, that is on the spherical recess 7a of the plunger 5a, the conical end of the plunger 5a is pushed forward into the bore at the instrument connection 150 and is pressed on here. As long as the pressure of the fluid prevails there is a positive fit connection. As soon as the fluid in the control space is no longer under pressure, the plunger 5a is pressed back by the axially running compression spring 9 and the bore at the instrument connection is again made free. By way of this the preparation of the instrument may be carried out in time intervals i.e. sequentially.

Figure 2:
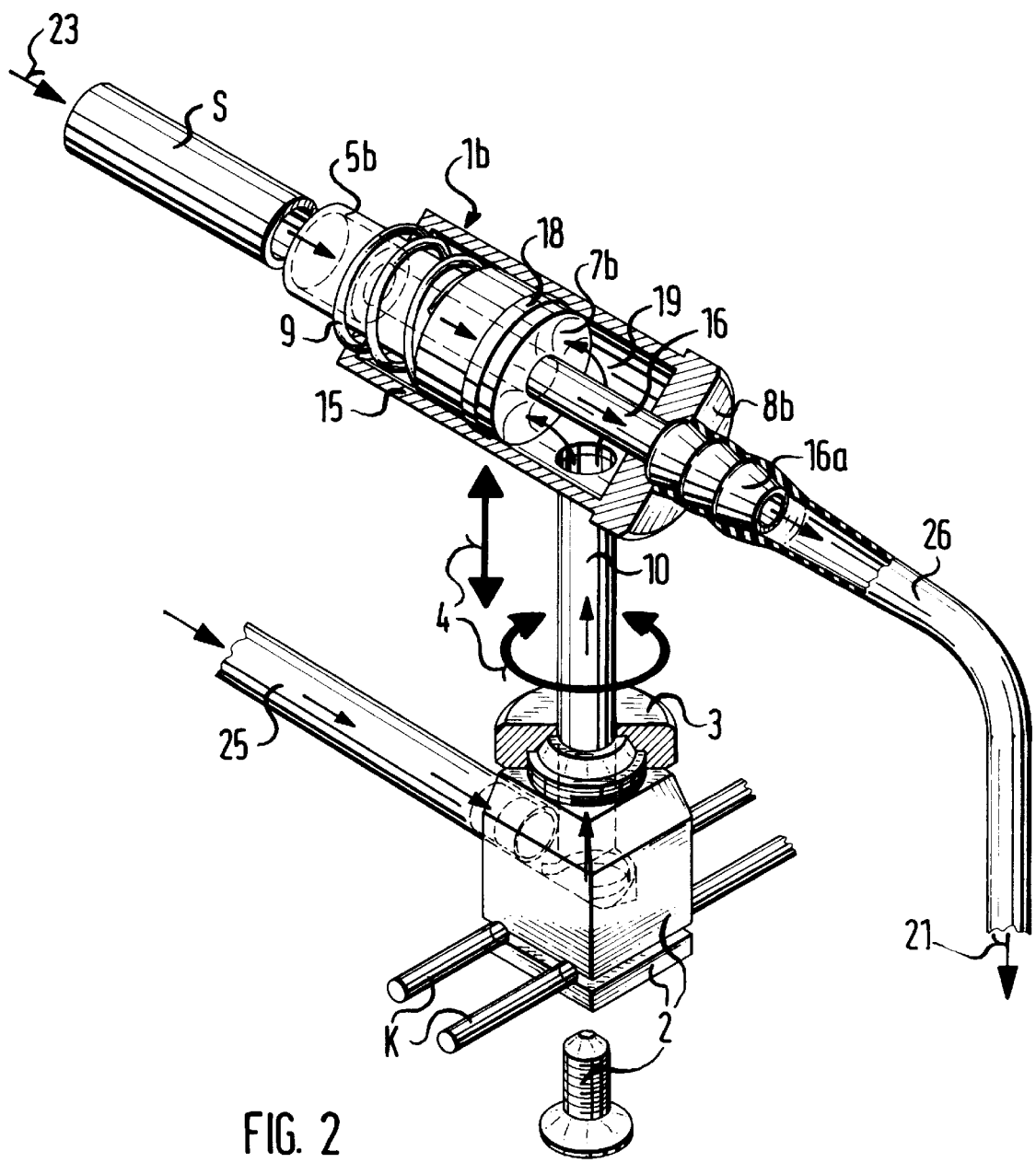
FIG. 2 is applied and which is particularly suitable for the evaluation of the quality of preparation, and FIG. 5 the form of a tubing connection with a variable sealing sleeve for the temporary docking on instrument shanks having different outer diameters.

The second embodiment 1b of the rinsing device according to the invention shown in FIG. 2 differs from the first embodiment form 1a in FIG. 1 in the design of the injector nozzle and in the separation of the rinsing fluid flow circuit and the control fluid flow circuit. The plunger 5b, differently from the plunger 5a in FIG. 1, does not run conically but forms at its distal end a cylindrical extension, whose inner lumen is for example adapted to the outer diameter of a shank tube S of an endoscope. If the control fluid supplied through the admission tube 25 is put under pressure, then the plunger 5b is pressed over the shank tube end and sealingly closes this towards the outside. The rinsing fluid flow in FIG. 2 runs from the shank tube S through the passage bore of the plunger and through a rinsing fluid tube 16 which is connected here and which leads through the control space 19 and the screw cap 8b to the outside and here forms a connection piece 16a for a tubing conduit 26 which is connected to a collector channel indicated by the arrow 21 or to a reservoir for the rinsing fluid. The rinsing device shown in FIG. 2 is thus used for leading away the rinsing fluid from the flushed channel, i.e. out of the instrument exit. Here too the plunger 5b must be aligned centrically to the channel opening at the shank tube end.

In order to produce a good sealing connection between the outer wall of the shank tube and the inner wall of the cylindrical extension at the distal end of the plunger 5b, a circumferential sealing lip may lie in this extension. The rinsing fluid 23 flowing into and out of the shank tube may also be suctioned into the collector channel 21 as an additional measure. Furthermore the application of the second embodiment type shown in FIG. 2 is not limited to the discharge of the rinsing fluid. The direction of the rinsing fluid flow indicated with the arrows may also be reversed so that rinsing fluid from the reservoir (arrow 21) may be injected through the rinsing fluid tube 16 and the plunger 5b into the shank tube end.

Figure 3:
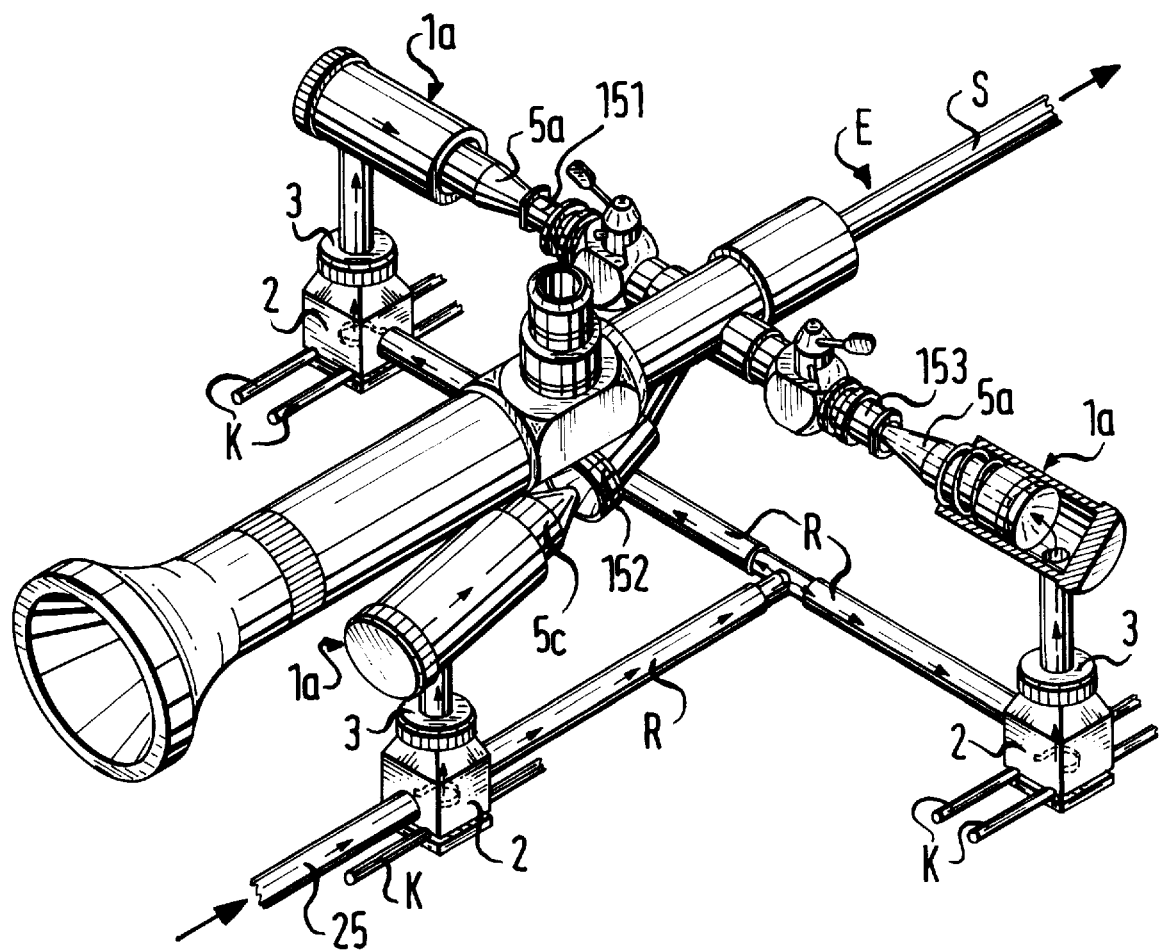

FIG. 3 shows a first application example of the rinsing device according to the invention in which connections and channels of an endoscope E are rinsed. From FIG. 3 it can be recognized that a rinsing device with three injector nozzles 1a of the type shown in FIG. 1 is applied. The three injector nozzles are fastened to the fastening devices 2 stationarily on the trellis of a rinsing basket K and are connected amongst each other by way of a common tube conduit R. A supply tubing 25 supplies rinsing and control fluid, put under pressure, which discharges through the instrument shank S. The individual injector nozzles 1a are, in the example shown, docked on three end connections 151–153 of the endoscope E. It is further shown that the shape and dimensions of the plunger are adapted to the connections of the instrument. Thus for docking onto the end connections 151 and 153 the plunger 5a of a first type is applied and for the docking onto the end connection 152 a plunger 5c of a second type (with a larger diameter) is applied. Also this rinsing device is fixedly assigned to the rinsing basket K and is specific to the instrument.

The rinsing fluid admission common to the three injector nozzles causes the three instrument accesses or end connections 151–153 to be essentially controlled and rinsed simultaneously. Alternatively to the common supply tubing, separate admissions for each injector nozzle may also be realized, if this is required, so that the individual instrument accesses can be docked and rinsed separately and independently from one another.

Figure 4:
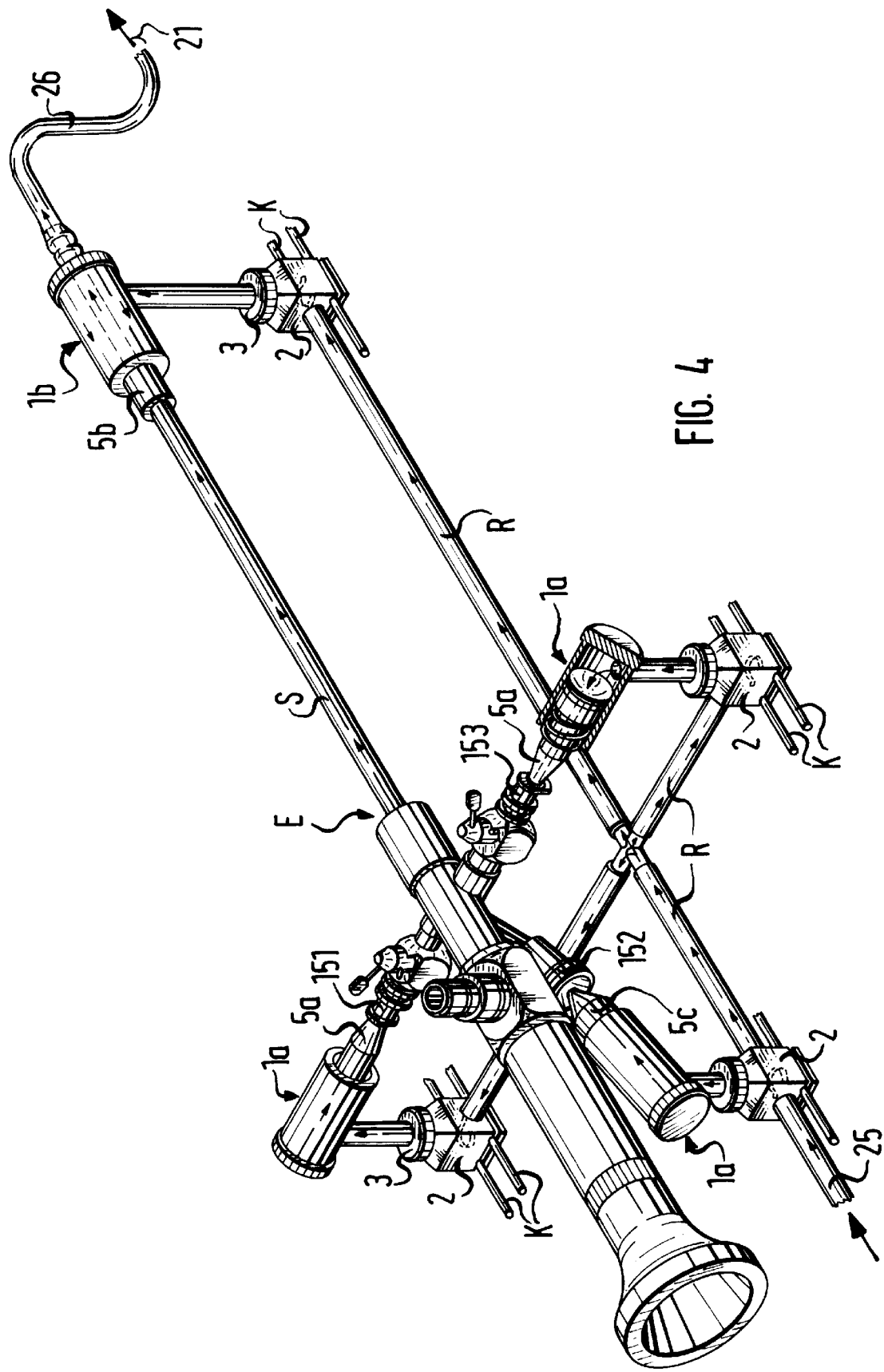

Also with the second application example shown in FIG. 4 the rinsing device according to the invention is used for rinsing the end connections and channels of an endoscope E.

This arrangement likewise remains fixedly assigned to a given rinsing basket K and a given instrument. The left and lower part of the device is identical to the arrangement according to FIG. 3. Furthermore at the end of the endoscope shank S there is docked an injector nozzle 1b of the embodiment type shown in FIG. 2 and a rinsing fluid discharge 26 is connected to a reservoir or collector channel indicated by an arrow 21. Thus in operation in the left part of the rinsing device of FIG. 4 the rinsing fluid circuit and the control fluid circuit are the same, whilst in the right part, i.e. in the case of the injector nozzle 1b which is docked onto the shank end of the endoscope, the rinsing fluid circuit and control fluid circuit are separated so that here the whole rinsing fluid fed into the instrument may be discharged. The branched tube conduit system for supplying pressurized fluid is indicated at R. It is furthermore to be noted that the rinsing device in FIG. 4 comprises two different types of fastening devices 2 and 2' of which the device 2 has only one fluid admission and the fastening device 2' has a fluid admission and a fluid discharge diametrically opposite.

Although in the above description of the application of the rinsing device shown in FIG. 4, the part docked on the shank end of the endoscope E is described as an "injector nozzle", since its design embodiment corresponds to that shown in FIG. 3, its function is not the injection but the draining of rinsing fluid. With regard to FIG. 2 it has already been explained that the injector nozzle may be employed for flowing through rinsing fluid in both directions which are opposite to one another.

Figure 5A:
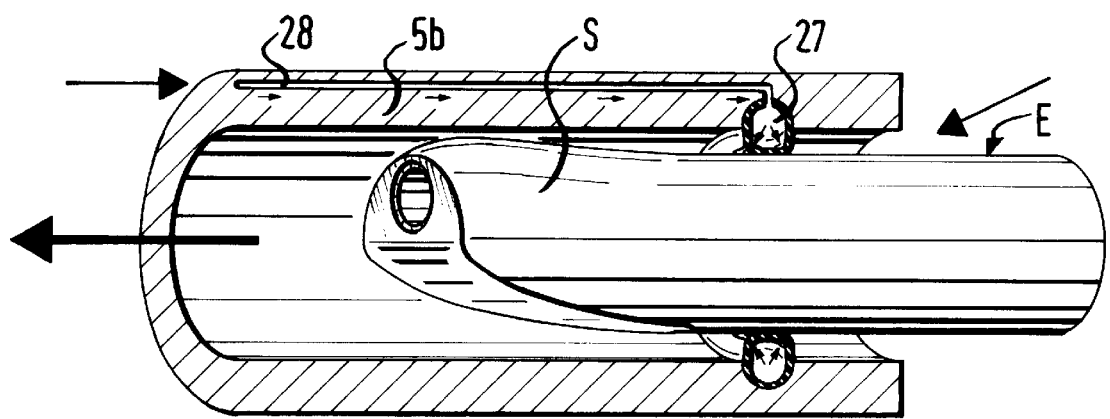
Figure 5B:
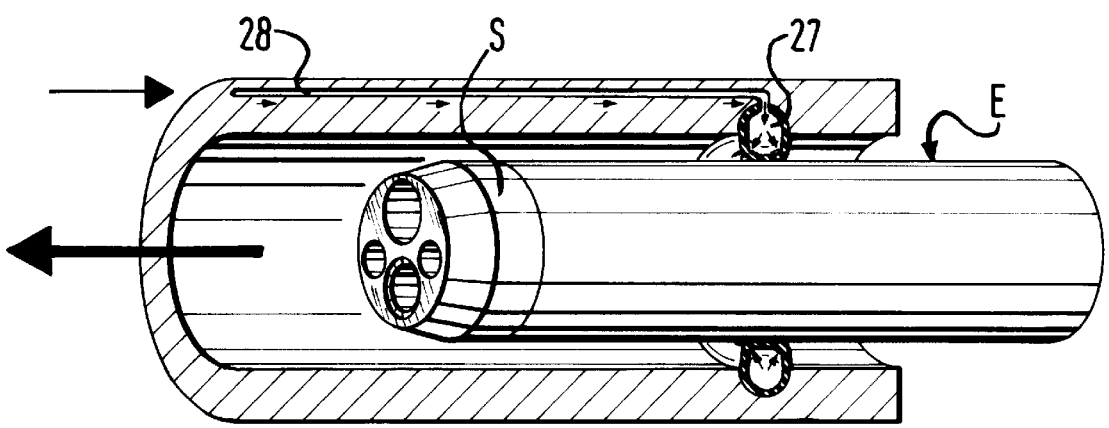

FIG. 5 shows the injector nozzle for receiving the distal shaft end of a medical instrument E, in particular of an endoscope. The sealing of the outer instrument shank S for instruments with different shank diameters and different shapes of shank is according to FIG. 5 designed with a hollow annular seal 27 which by way of a fluid impinged by pressure and supplied via the channel 28, is adapted to the outer circumference of the instrument shank. With this flexible instrument shanks may also be securely sealed towards the outside. Pressurized air or water may be controllably led through the channel 28 into the annular seal until a circumferentially fitting sealing is produced. This possibility may be applied satisfying the requirements of the injector device as well as the receiver device. The complete control for the elements employed may also here be machine controlled via valves in a program dependent manner.

It is desirable to be able to obtain a proof as to whether the rinsed instrument channel during the mechanized preparation is sufficiently flushed according to the instruction, volume and time. For this the actual fluid quantity delivered through the instrument shank only can serve the verification progress with an unfalsifiable determination of volume. It is therefore important that the device with the injector nozzle 1b for collecting the rinsing fluid from the instrument shank only receives that fluid flow which actually flows through the shank. Only so can an error free evaluation of the quality of preparation be achieved. For this it is required that the desired throughput and the measured throughput are compared and evaluated, which is why the supplied as well as the collected fluid quantity must be measured.

With the application example shown in FIG. 4 during the rinsing phases simultaneously also the collecting device or the reservoir 21 is operated via the injector nozzle 1b which is sealingly pushed over the distal end of the instrument shank. Here the injector nozzle shown in an enlarged scale in FIG. 5 may be used in accordance with FIG. 4. With this a secure and controllable collecting possibility is created. If the fluid supply is interrupted and the pressure falls, the collecting device, i.e. the plunger of the injector nozzle 1b, is pushed back into the home position so that the shank in this region is freely accessible and can be completely prepared. By way of a comparison measurement between the supply and discharge or by way of a determination in volume the successful preparation may be documented. When the throughflow of a channel is not adequate the instrument concerned may otherwise be registered in order to single it out and where appropriate it may be prepared separately.

In the following, once again the essential conditions for an exact evaluation of the quality of preparation are indicated. All fluid flow volumes flowing through the channels must be directly and individually measured and subsequently documented, wherein it must be secured that the rinsing fluid fed to the evaluation is collected in an unadulterated manner, i.e. without losses and without additionally collected splashed water. Furthermore the positive fit connection between the shank end and the injector nozzle 1b may only be present during the flowthrough. Finally the collecting device, i.e. the plunger of the injector nozzle 1b, must automatically be pushed back in the predetermined phases in which no rinsing is provided, so that the instrument or its shank end is cleared for a complete rinsing around for the cleaning or disinfection.

The operations of the injector nozzles controlled in chronological intervals are usefully effected in a program controlled manner so that a rinsing or preparation program may be selected depending on the instrument to be prepared in each case. For this the fluid operating device comprises a time control unit or is connected to such. This program controlled time control unit may be realised e.g. in the form of a microprocessor.

With the above mentioned rinsing device according to the invention, in particular the following advantageous effects are achieved. All connections or rinsing connections on the medical instrument may with a standardized mechanized preparation according to the invention be prepared internally and externally without regions hidden from the rinsing. During the preparation all releasable connecting parts may be separated and the instrumentation may be fixed in receptacles which can be well rinsed through in special mountings of the rinsing baskets with point resting contact. The course of the preparation also completely includes the inner lumen of the shank tubes and guarantees a thorough and specifically directed flushing. i.e. cleaning and disinfection.

The disadvantage of a rigidly adapted tubing connection usual up to now, which is that by way of the slipping over or coupling of a tubing, in the covered region no complete preparation may be effected and thus here an increased risk of entrainment and transmission of germs arises, is avoided. Also critical regions may be kept accessible to the preparation medium during the whole preparation. Finally the quality of preparation whilst maintaining the above mentioned conditions may be unambiguously evaluated and documented.

Thus, while there have shown and described and pointed out fundamental novel features of the invention as applied to preferred embodiments thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. It is the intention, therefore, to be limited only as indicated by the scope of the claims appended hereto.

I claim:

1. An apparatus for rinsing a channel of a medical instrument with a fluid supplied by a fluid supply under a pressure, the medical instrument having a channel connector communicating with the channel, comprising:

a fluid injector for selectively forming a sealed connection with the channel connector for transferring fluid from the fluid supply thereto, said fluid injector comprising:

a hollow tubular housing having a central longitudinal axis, a proximal end, and a distal end sized and configured to selectively connect to the channel connector of the medical instrument;

an opening for receiving fluid supplied by the fluid supply; and a plunger movably disposed at least partially within said tubular housing, said plunger having a front portion, a rear portion, a fluid passage running axially therein, and being movable along the central longitudinal axis, wherein said front portion of said plunger is sized and configured to form a sealable connection with the channel connector of the medical instrument, such that when said tubular housing and said front portion of said plunger are axially aligned with the channel connector and fluid from the fluid supply is delivered into the housing, the pressure exerted by the fluid on said plunger is sufficient to cause said plunger to move along said central longitudinal axis of said housing into a sealed connection with the channel connector for delivery of the fluid through said fluid passage thereto.

2. The apparatus of claim 1, further comprising positioning means for selectively adjusting and retaining the spatial position and orientation of said fluid injector to facilitate alignment with the channel connector of the medical instrument.

3. The apparatus of claim 2, wherein said positioning means comprises:

an elongate member rotably attached to said fluid injector;

a base having a releasable clamping screw connector for receiving and retaining said elongate member, wherein when said screw connector is released, said elongate member is movable vertically and freely rotable to facilitate adjustment of height and rotational position of said fluid injector, and wherein when said screw connector is clamped said elongate member is retained in a fixed position; and means for releasably securing said base to a stationary surface to prevent free movement of the base therefrom.

4. The apparatus of claim 1 wherein said plunger is composed of substantially elastic material.

5. The apparatus of claim 1 wherein the channel connector of the medical instrument comprises an inner lumen, and wherein said front portion of said plunger comprises a substantially conical plug sized and configured for insertion into said inner lumen to form a sealed connection therewith.

6. The apparatus of claim 1, wherein said rear portion of said plunger comprises a hollow concave region conically broadening from said fluid passage for facilitating the flow of fluid therein.

7. The apparatus of claim 1, wherein said front portion of said plunger comprises a hollow sleeve sized and configured to fit over the channel connector of the medical instrument to form a sealed connection therewith.

8. The apparatus of claim 7, further comprising:

a hollow elastic toroidal ring seal disposed circumferentially within said hollow sleeve;

a channel disposed longitudinally in a wall of said hollow sleeve and communicating with said toroidal ring seal for delivering and removing one of air or water to said toroidal ring seal;

means for providing one of air or water to said toroidal ring seal when said hollow sleeve is fitted over the channel connector of the medical instrument, to inflate said toroidal ring seal to form a sealed connection between said hollow sleeve and the channel connector; and means for removing said one of air or water from said toroidal ring seal when said hollow sleeve is removed from the channel connector to facilitate rinsing of the channel connector.

9. The apparatus of claim 1, wherein a portion of said plunger that is disposed within said housing comprises a circumferential sealing lip of elastic material, such that a sealed control space is formed between said rear portion of said plunger and said housing proximal end.

10. The apparatus of claim 9, further comprising means positioned in said housing for moving said plunger toward said proximal end in opposition to the pressure exerted on said plunger by the fluid supplied by the fluid supply, such that when the fluid pressure in said control space exceeds a first predetermined level, said plunger is pushed by the fluid toward said distal end of said housing into sealed connection with the channel connector, and when the fluid pressure in said control space falls below a second predetermined level said moving means pushes said plunger back toward said proximal end.

11. The apparatus of claim 1, wherein said plunger is removably positioned within said housing such that said plunger is interchangeable with at least one other plunger of a plurality of variously configured plungers.

12. The apparatus of claim 1, wherein said housing comprises a releasable cover cap positioned at one of said proximal and said distal ends.

13. The apparatus of claim 1, further comprising at least two fluid injectors, wherein when a sealed connection between said plunger of a second one of said at least two fluid injectors and another one of the channel connector is formed, the fluid delivered from at least one other fluid injection device into the medical instrument for rinsing the instrument flows into said housing of said second fluid injector device from said another one of the channel connector of the medical instrument and through said centrally axially running channel, said second fluid injector device thereby serving as a fluid collection device and comprising means for collecting fluid flowing into said second fluid injector device housing from the medical instrument.

14. The apparatus of claim 13, wherein said fluid collection means comprises:

a cover cap having a central bore, said cover cap being positioned at said proximal end of said housing;

a rinsing tube led through said bore for collecting rinsing fluid received from one of the channel connector of the medical instrument and through said centrally axially running channel;

a collector reservoir for collecting and storing the rinsing fluid; and a connection conduit for connecting said rinsing tube to said collector reservoir.

* * * * *